United States Patent [19]

Mross et al.

[11] 4,278,562

[45] Jul. 14, 1981

[54] MANUFACTURE OF AN ETHYLENE OXIDE CATALYST

[75] Inventors: Wolf D. Mross; Eckart Titzenthaler, both of Ludwigshafen; Juergen Koopmann, Neustadt; Matthias Schwarzmann; Volker Vogt, both of Limburgerhof, all of Fed. Rep. of Germany

[73] Assignee: BASF Aktiengesellschaft, Fed. Rep. of Germany

[21] Appl. No.: 959,684

[22] Filed: Nov. 13, 1978

[30] Foreign Application Priority Data

Nov. 19, 1977 [DE] Fed. Rep. of Germany ....... 2751767
May 11, 1978 [DE] Fed. Rep. of Germany ....... 2820520

[51] Int. Cl.$^3$ .................. B01J 31/02; B01J 23/50; B01J 23/96; C07D 303/04
[52] U.S. Cl. .................................. 252/430; 252/412; 252/414; 252/476; 260/348.34
[58] Field of Search ................ 252/412, 414, 476, 430

[56] References Cited

U.S. PATENT DOCUMENTS

| 4,007,135 | 2/1977 | Hayden et al. | 252/476 |
| 4,033,903 | 7/1977 | Maxwell | 252/476 |
| 4,123,385 | 10/1978 | Rebsdat et al. | 252/412 |
| 4,125,480 | 11/1978 | Maxwell | 252/414 |
| 4,168,247 | 9/1979 | Hayden et al. | 252/476 |

FOREIGN PATENT DOCUMENTS 2519599 7/1976 Fed. Rep. of Germany .

*Primary Examiner*—P. E. Konopka
*Attorney, Agent, or Firm*—Keil & Witherspoon

[57] ABSTRACT

A catalyst for the manufacture of ethylene oxide, giving improved yield and having a long life, based on an alkali metal-modified silver catalyst on an oxide carrier is obtained by providing the silver-containing catalyst, in the reduced state, with the alkali metal by applying an alcoholic alkali metal salt solution which also contains an organic oxygen compound or nitrogen compound which forms complexes with silver ions.

2 Claims, No Drawings

MANUFACTURE OF AN ETHYLENE OXIDE CATALYST

The present invention relates to an improved catalyst for the manufacture of ethylene oxide which contains, on a porous carrier, finely divided silver together with sodium and/or lithium as well as potassium and/or rubidium and/or cesium (referred to as heavy alkali metals), and in order to manufacture which silver, with or without sodium and/or lithium, in the form of the relevant salts, is first applied to the carrier and the material is heated (activated) in the conventional manner, whilst in a subsequent treatment a salt of a heavy alkali metal together with, for example, an amine and/or ammonia, is also applied. The term heavy alkali metal here means the elements potassium, rubidium and cesium.

It is known that the selectivity, for the formation of ethylene oxide from ethylene and oxygen, of an old silver catalyst (German Published Application DAS No. 2,519,599) or a silver catalyst stabilized by a heat treatment (U.S. Pat. No. 4,033,903) can be improved by after-treating the catalyst with, in particular, rubidium or cesium. The after-treatment is carried out by impregnating a silver catalyst which has been used for a certain length of time for the synthesis of ethylene oxide and has in the process undergone stabilization, with a solution of one of the heavy alkali metals in a polar organic solvent (methanol, for example, has been proposed), the treatment being carried out in the synthesis reactor. To improve the solubility of the alkali metal salt, the solvent can contain up to about 10% of water.

If a silver catalyst which has not been used and not been stabilized is treated in this way, virtually no improvement in selectivity is achieved, or the improvement obtained is less than that achieved when employing a previously used or stabilized catalyst (see Comparative Example 1). It is an object of the present invention to improve the catalyst selectivity.

We have found that this object is achieved and that a catalyst of improved selectivity compared to catalysts obtained by conventional after-treatment processes is obtained if the after-treatment is carried out with a solution which contains a salt of a heavy alkali metal, i.e. potassium but especially rubidium and/or cesium, a polar organic solvent, especially an alcohol of 1 to 4 carbon atoms, with or without a small amount of water, and, according to the invention, an organic compound which forms complex salts, via an oxygen atom and/or a nitrogen atom, with silver-(I) ions.

Using the solution according to the invention, a catalyst having excellent selectivity can also be produced by treating an unused catalyst, ie. a catalyst intermediate. Accordingly, the after-treatment need not be carried out in the synthesis reactor; instead, the preparation of the silver catalyst, including the after-treatment, can be carried out in a conventional apparatus suitable for the preparation of supported catalysts. Such apparatuses, and their use, are described, for example, in Ullmann's Enzyklopädie der technischen Chemie, 3rd edition, volume 13, pages 517 et seq.

The terms "used catalyst" and "unused, but not after-treated catalyst" as used in the present specification mean a catalyst which contains, on a commercial carrier (e.g. aluminum oxide, silica or a silicate), for example from 2 to 12, especially from 5 to 10, percent by weight of silver, with or without up to 2 atom percent, based on the silver content, of sodium or lithium or a mixture of these, and with or without small amounts (less than about 0.1 atom percent) of heavy alkali metals, remaining from an earlier treatment.

The improvement achievable according to the invention is attained regardless of whether the catalyst to be treated contains, or does not contain, sodium or lithium but it is particularly advantageous if the catalyst resulting from the after-treatment contains (in each case based on silver) from about 0.1 to 2 atom percent of sodium and/or lithium and either from 0.05 to 0.35 atom percent of potassium, from 0.003 to 0.25 atom percent of rubidium or from 0.0005 to 0.2 atom percent of cesium, or an appropriate amount of a mixture of the last-mentioned alkali metals.

To prepare solutions which may be used according to the invention, the concentration of heavy alkali metals is generally chosen so that after part of the solution has been absorbed by the catalyst and the non-absorbed part has been removed, the amount of alkali metals which is effective according to the invention is present on the catalyst.

As disclosed in Gmelins Handbuch der anorganischen Chemie (8th edition, volume: Silver, part B 6, Springer-Verlag Berlin, Heidelberg, New York), compounds which contain oxygen or nitrogen act as complexing agents for silver. Compounds to be excluded are of course those which are known to damage silver catalysts, for example phosphorus compounds and sulfur compounds.

Examples of suitable strongly complexing oxygen compounds are those which contain several oxygen atoms in a configuration such that they can form coordination complexes with silver. For example, suitable oxygen compounds are diketones, eg. diacetyl, ethyl acetoacetate and acetylacetone, and multiple ethers, in particular the crown ethers.

Examples of nitrogen compounds which are strongly complexing are amines, ammonia and cyano compounds (nitriles) e.g. acetonitrile. For the purposes of the invention, preferred amines are aliphatic means, ie. monoalkylamines, dialkylamines and trialkylamines, alkanolamines and compounds with a plurality of amine groups, eg. alkylenediamines, piperazines and the like.

The complexing agents are employed in an amount of, for example, up to 30% by volume, based on the solution intended for the after-treatment. Amounts of from 0.1 to 10% by volume are advantageous.

The treated catalyst or intermediate is converted to the active form in the conventional manner by heating, in the presence or absence of the conventional gaseous reaction mixture of ethylene and oxygen.

EXAMPLE 1

139 g of silver nitrate are dissolved in a mixture of 120 g of sec.-butylamine and 4 g of an aqueous solution of 0.57 g of lithium nitrate and 0.38 g of sodium nitrate. The solution is made up to a volume which corresponds to the liquid absorption capacity of the intended carrier. 1 kg of aluminum oxide in bead form (a carrier from NORTON, Akron, U.S.A., type SA 5,551) is impregnated with the prepared solution. The resulting catalyst intermediate is stored for one day at room temperature and then dried in a through-circulation dryer at 220° C., whereby the silver is deposited on the carrier. The catalyst contains 8.0 percent by weight of silver, 0.55 atom percent of sodium and 1.0 atom percent of lithium.

The atom percentages are based on silver. The catalyst is designated A.

10 ml of comminuted catalyst A are introduced into a test reactor of 5 mm internal diameter and 30 l (S.T.P)/h of a gas mixture consisting of 28% of ethylene, 8% of oxygen, 2 ppm of vinyl chloride, remainder nitrogen, are passed through the catalyst under 15 bar pressure. The temperature is regulated to give 50% oxygen conversion. When, after a few days, a constant activity level has been reached, the experiment is discontinued and the catalyst is impregnated in the reactor, at room temperature, with a methanol solution containing 400 ppm of $CsNO_3$, 5% of sec.-butylamine and 0.5% of water. After treatment for one hour, the excess solution is drained off and the catalyst is dried by heating the reactor and passing nitrogen through it. The catalyst treated in this way is designated B. An activity and selectivity test at 50% $O_2$ conversion is carried out with the gas mixture used previously. The result is included in Table 1.

EXAMPLE 2

100 ml of catalyst A are impregnated with a methanol solution containing 350 ppm of CsOH and 2% of concentrated aqueous ammonia and are then dried in a through-circulation dryer at 220° C. The resulting catalyst (designated C) is subjected to the activity and selectivity test (Table 1).

EXAMPLE 3

The procedure described above is followed; the impregnating solution contains 330 ppm of $CsCO_3$, 2% of ethylenediamine and 1% of concentrated aqueous ammonia in methanol; the catalyst is designated D. The result of the performance test is shown in Table 1.

COMPARATIVE EXAMPLE 1

The catalyst is prepared as described in Example 1, but the sec.-butylamine is omitted from the impregnating solution. This gives catalyst M, Table 1.

COMPARATIVE EXAMPLE 2

The catalyst is prepared as described in Example 2, but the ammonia is omitted from the impregnating solution. This gives catalyst N, Table 1.

TABLE 1

| Catalyst | Comparative temperature+ °C. | Selectivity+ % |
| --- | --- | --- |
| B | 221 | 81.5 |
| C | 217 | 80.5 |
| D | 218 | 80.5 |
| M (comparison) | 223 | 78.5 |
| N (comparison) | 218 | 77.5 |
| A (comparison) | 217 | 76.5 |

+at 50% oxygen conversion

EXAMPLE 4

100 ml of catalyst A as obtained in Example 1 are impregnated with a methanol solution containing 350 ppm of CsOH and 2.5% by volume of acetonitrile, and are then dried at 220° C. in a through-circulation dryer. The catalyst, designated E, is subjected to the activity and selectivity test (Table 2).

EXAMPLE 5

The silver catalyst is prepared as described in Example 1, but the impregnating solution contains only lithium nitrate (i.e. no sodium nitrate). The further treatment is also carried out as described above; the aftertreatment solution contains 350 ppm of $NaNO_3$ in addition to 350 ppm of $CsNO_3$. The catalyst is designated F (Table 2).

EXAMPLE 6

The catalyst is prepared as described in Example 4, but 1% by volume of acetylacetone is employed instead of acetonitrile. The catalyst is designated G (Table 2).

EXAMPLE 7

The catalyst is prepared as described in Example 4, but 3% by volume of dicyclohexyl-18-crown-6 (crown ether) are used instead of acetonitrile. This gives catalyst H (Table 2).

TABLE 2

| Catalyst | Comparative temperature °C. | Selectivity % |
| --- | --- | --- |
| E | 218 | 81.5 |
| F | 214 | 82.0 |
| G | 224 | 81 |
| H | 225 | 81 |

We claim:

1. A process for the preparation of a catalyst on a carrier for the manufacture of ethylene oxide by reaction of ethylene with oxygen in the gas phase, which catalyst contains from about 2 to 12% of elementary silver and alkali metals or their compounds, comprising:
applying at least one of the alkali metals potassium, rubidium or cesium to the catalyst carrier by treating the catalyst which already contains silver in the reduced form, with or without sodium and/or lithium, with a solution of a compound of potassium, rubidium and/or cesium which contains 0.1 to 10% by volume of a diketone which forms complex salts, via an oxygen atom with silver-(I) ions, and using the solution in such amount that the solution absorbed by the catalyst corresponds to (based on silver) from 0.05 to 0.35 atom percent of potassium, from 0.003 to 0.25 atom percent of rubidium or from 0.0005 to 0.2 atom percent of cesium or to a corresponding amount of a mixture of these alkali metals, taking due account to any amounts of alkali metals which may already be present on the catalyst.

2. The process as set forth in claim 1, wherein a diketone selected from the group consisting of diacetyl, ethyl acetoacetate, and acetylacetone is used as the compound which forms complex salts.

* * * * *